(12) United States Patent
Valkirs

(10) Patent No.: US 6,348,318 B1
(45) Date of Patent: Feb. 19, 2002

(54) METHODS FOR CONCENTRATING LIGANDS USING MAGNETIC PARTICLES

(75) Inventor: Gunars E. Valkirs, Escondido, CA (US)

(73) Assignee: Biosite Diagnostics, San Diego, CA (US)

(*) Notice: Subject to any disclaimer, the term of this patent is extended or adjusted under 35 U.S.C. 154(b) by 0 days.

(21) Appl. No.: 09/054,918

(22) Filed: Apr. 3, 1998

Related U.S. Application Data

(60) Provisional application No. 60/044,292, filed on Apr. 4, 1997.

(51) Int. Cl.[7] .................... G01N 33/543; G01N 33/553; G01N 33/569
(52) U.S. Cl. ........................ 435/7.1; 435/7.2; 435/7.32; 435/7.35; 435/7.37; 435/7.92; 435/7.93; 435/7.94; 435/975; 436/518; 436/526; 436/806; 436/824
(58) Field of Search ................................ 435/7.5, 7.92, 435/7.93, 7.94, 7.32, 7.35, 7.37, 7.2, 7.1, 975; 436/518, 526, 824, 806, 541

(56) References Cited

U.S. PATENT DOCUMENTS

| | | | |
|---|---|---|---|
| 4,533,630 A | 8/1985 | Wilkins et al. ................. 435/7 |
| 4,554,088 A | 11/1985 | Whitehead et al. ...... 252/62.54 |
| 4,628,037 A | 12/1986 | Chagnon et al. ............. 436/526 |
| 4,659,678 A * | 4/1987 | Forrest et al. ............... 436/512 |
| 4,672,040 A | 6/1987 | Josephson ................... 436/526 |
| 4,695,392 A | 9/1987 | Whitehead et al. ...... 252/62.54 |
| 4,695,393 A | 9/1987 | Whitehead et al. ...... 252/62.54 |
| 5,332,679 A * | 7/1994 | Simons et al. ............... 436/518 |
| 5,429,927 A | 7/1995 | Afseth et al. ................. 435/7.2 |
| 5,646,001 A | 7/1997 | Terstappen et al. ........ 435/7.21 |

FOREIGN PATENT DOCUMENTS

| | | |
|---|---|---|
| WO | WO91/01368 | 2/1991 |
| WO | WO91/15766 | 10/1991 |
| WO | WO92/17609 | 10/1992 |
| WO | 94/02016 * | 2/1994 |

OTHER PUBLICATIONS

R.D. Dunn et al., "Antigen Binding and Cytotoxic Properties of a Recombinant Immunotoxin Incorporating the Lytic Peptide, Melittin," Immunotechnology (Amsterdam) (1996) 2(3): 229–240 (Chemical Abstracts Service AN 97:22749 Biosis).
Parmley & Smith, *Gene* (1988) 73: 305–318.
Kerr et al. *J. Appl. Bacteriol.* (1992) 72: 302.
Tsang et al. *Infect. Immun.* (1987) 55: 211.
Luk et al. *J. Biol. Chem.* (1991) 266: 23215.

* cited by examiner

*Primary Examiner*—David Saunders
(74) *Attorney, Agent, or Firm*—Townsend and Townsend and Crew LLP

(57) ABSTRACT

This invention provides methods, compositions and kits for concentrating target ligands, including microorganisms, from samples, including biological samples. The methods involve the use of magnetic particles to concentrate the target analytes. Also provided are methods, compositions and kits for detecting the presence of target ligands in samples.

15 Claims, 4 Drawing Sheets

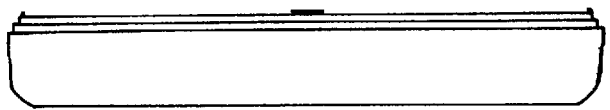
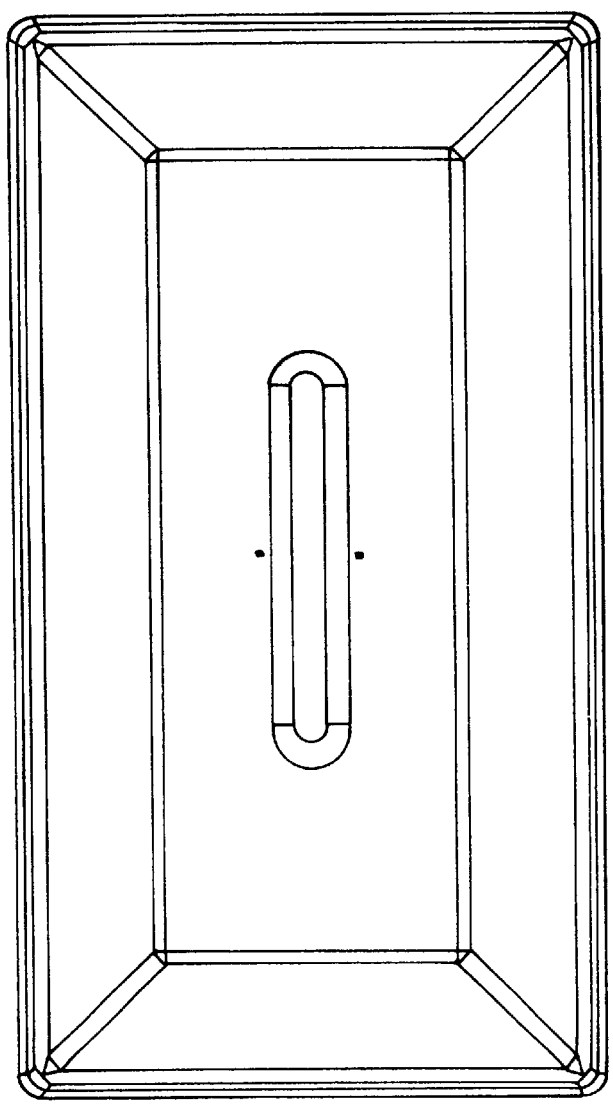
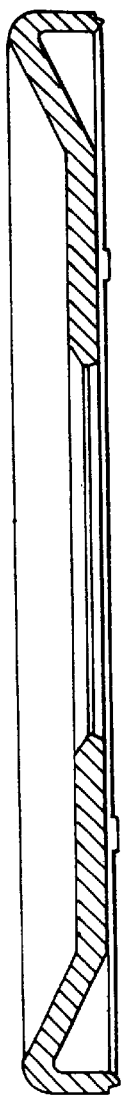

```
                           SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
         (A) LENGTH: 8 amino acids
         (B) TYPE: amino acid
         (C) STRANDEDNESS: <Unknown>
         (D) TOPOLOGY: linear (ii) MOLECULE TYPE: peptide (xi) SEQUENCE DESCRIPTION: SEQ ID NO: 1:

Asp Tyr Lys Asp Asp Asp Asp Lys
1               5

(2) INFORMATION FOR SEQ ID NO: 2:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO: 2:

GACTACAAGG ACGACGATGA CAAG                                               24

(2) INFORMATION FOR SEQ ID NO: 3:

(i) SEQUENCE CHARACTERISTICS:
         (A) LENGTH: 4 amino acids
         (B) TYPE: amino acid
         (C) STRANDEDNESS: <Unknown>
         (D) TOPOLOGY: linear (ii) MOLECULE TYPE: peptide (xi) SEQUENCE DESCRIPTION: SEQ ID NO: 3:

Asp Tyr Lys Asp
1

(2) INFORMATION FOR SEQ ID NO: 4:

(i) SEQUENCE CHARACTERISTICS:
         (A) LENGTH: 5 amino acids
         (B) TYPE: amino acid
```

```
            (C) STRANDEDNESS: <Unknown>
            (D) TOPOLOGY: linear (ii) MOLECULE TYPE: peptide (xi) SEQUENCE DESCRIPTION: SEQ ID NO: 4:

Asp Tyr Lys Asp Glu
1               5

(2) INFORMATION FOR SEQ ID NO: 5:

(i) SEQUENCE CHARACTERISTICS:
            (A) LENGTH: 10 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 5:

Tyr Pro Tyr Asp Val Pro Asp Tyr Ala Ser
1               5                   10
```

METHODS FOR CONCENTRATING LIGANDS USING MAGNETIC PARTICLES

CROSS-REFERENCE TO RELATED APPLICATIONS

This application claims benefit of U.S. provisional application Ser. No. 60/044,292, filed Apr. 4, 1997, and is related to U.S. patent applications Ser. Nos. 08/832,935, now U.S. Pat. No. 5,965,375, Ser. No. 08/832,985, now U.S. Pat. No. 6,057,098, and Ser. No. 08/835,159, each of which was filed on Apr. 4, 1997. These applications are incorporated herein by reference in their entireties for all purposes.

BACKGROUND OF THE INVENTION

1. Field of the Invention

This invention pertains to the field of methods for concentrating target ligands and microorganisms from biological samples using binding moieties that are reversibly immobilized to magnetic particles. The methods provide highly sensitive means for concentrating and detecting target ligands and microorganisms that are present in a sample at very high dilution.

2. Background

The use of magnetic particles for concentrating target ligands, including microorganisms, from samples provides a convenient purification method that has several advantages over other methods such as gravitational or centrifugal separation. See, e.g., U.S. Pat. Nos. 4,628,037, 4,672,040, 4,695,392, and 4,695,393 for a description of magnetic particles and their use in separations. A target ligand that had been concentrated by use of magnetic beads would generally be detected while still associated with the beads. However, the presence of the magnetic beads associated with the concentrated target ligands can hinder detection of the target ligand. Nonspecific binding to the magnetic beads would limit the sensitivity of such methods. As a sufficient number of beads were added to a sample to bind all or most of the target ligand in the sample, the nonspecific binding to the beads increased, thus decreasing sensitivity. If fewer beads were used to decrease nonspecific binding, the sensitivity would also decrease because less than substantially all of the target ligand would be captured. Thus, the signal to noise ratio of these assays was relatively constant, placing a limit on sensitivity.

Thus, a need exists for a magnetic separation method for concentrating target ligands that is able to achieve a high degree of concentration of the target ligand. The present invention fulfills this and other needs.

SUMMARY OF THE INVENTION

The present invention provides methods, compositions, and kits for concentrating a target analyte in a test sample using magnetic beads. The method involves adding to the sample a target analyte binding moiety that specifically binds to the target analyte to form a target complex comprising the target analyte and target analyte binding moiety, and adding to the sample a magnetic bead to which is attached a capture moiety that specifically binds to the target analyte binding moiety to form a magnetic bead-bound target complex. A magnetic field is applied to the sample to collect the magnetic bead-bound target complex, after which the target complex is dissociated from the magnetic bead, thereby providing a concentrated target analyte. The target analyte binding moiety and the magnetic bead can be added to the sample simultaneously, or one can be added prior to the other.

In a preferred embodiment, the binding between the target analyte binding moiety and the target analyte is reversible under mild conditions, so that the target analyte binding moiety retains the ability to bind to the target analyte after dissociation. If the dissociation conditions also cause the target analyte binding moiety and the target analyte to dissociate, then following separation of the magnetic beads, the concentrated target analyte solution can be modified so that the target analyte binding moiety and the target analyte can immediately reassociate. The target analyte binding moiety and the target analyte typically remain in contact with each other during and after the dissociation step, and the target analyte can remain associated with the target analyte binding moiety throughout the dissociation step.

In another embodiment, the invention provides methods, compositions, and kits for detecting a target analyte in a sample. The methods involve the steps of a) adding to the sample a target analyte binding moiety that specifically binds to the target analyte, to form a target analyte/binding moiety complex; b) adding to the sample a magnetic bead to which is attached a capture moiety that specifically binds to the target analyte binding moiety, to form a complex comprising the target analyte binding moiety, the target analyte, and the magnetic bead; c) separating the complex from the sample by applying a magnetic force to the sample; d) dissociating the target analyte/binding moiety complex from the magnetic bead and removing the magnetic bead from the solution containing the binding peptide-target analyte complex; and e) detecting the presence of the target analyte/binding moiety complex.

In one embodiment, the detection step involves an immunoassay. The immunoassay can be performed by applying the solution containing the target analyte binding moiety-target analyte complex to a solid support upon which is immobilized an anchor moiety that specifically binds to an epitope of the target analyte; applying a detection moiety that specifically binds to a hapten present on the target analyte binding moiety; and detecting the label. The target analyte epitope to which the target analyte binding moiety binds can be the same as or different than the epitope to which the anchor moiety binds.

The invention also provides kits and devices for detecting a target analyte in a sample. The kits can include a target analyte binding moiety that is capable of specifically binding the target analyte and a plurality of magnetically responsive particles to which are attached a plurality of capture moieties that are capable of reversibly binding the target analyte binding moiety. The target analyte binding moiety can include a molecular tag to which the capture moiety binds. The kits can also include a detection moiety that is capable of binding to the molecular tag, control antigens, and the like.

BRIEF DESCRIPTION OF THE DRAWINGS

FIGS. 3A–3C show a top piece of an apparatus for performing an immunoassay for detection of a target analyte. FIG. 3A is a top view, showing an elongated well in the center. FIG. 3B is a section view of the top piece, showing a membrane that is ultrasonically welded to the underside of the top piece. FIG. 3C is an end view of the top piece of the apparatus.

FIG. 4A is a top view, FIG. 4B is a section view, and FIG. 4C is an end view of the bottom piece. To construct a complete apparatus, a bottom piece is joined to a top piece such as is shown in FIGS. 3A–3C.

DETAILED DESCRIPTION

Definitions

Figure 1:
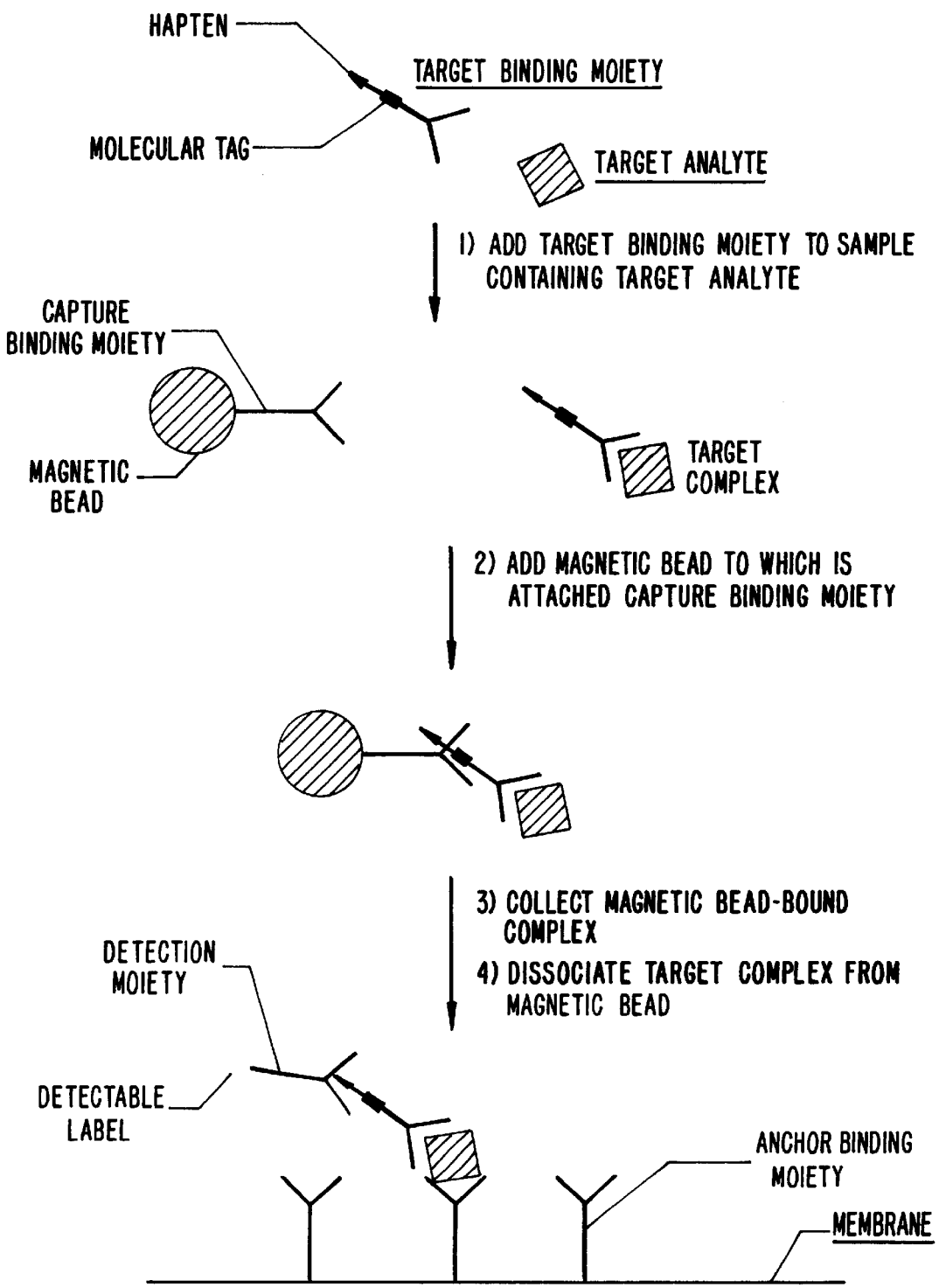
FIG. 1 shows a schematic diagram of a high sensitivity assay that is useful for detecting a target analyte.

The term "antibody," as used herein, includes, but is not limited to a polypeptide substantially encoded by an immunoglobulin gene or immunoglobulin genes, or fragments thereof which specifically bind and recognize an analyte (antigen). Examples include polyclonal, monoclonal, chimeric, and single chain antibodies, and the like. Fragments of immunoglobulins, including Fab fragments and fragments produced by an expression library, including phage display, are also included in the term "antibody" as used herein. See, e.g., Paul, *Fundamental Immunology*, 3$^{rd}$ Ed., 1993, Raven Press, New York, for antibody structure and terminology.

The phrases "specifically binds to" or "specifically immunoreactive with", when referring to an antibody or other binding moiety refers to a binding reaction which is determinative of the presence of the target analyte in the presence of a heterogeneous population of proteins and other biologics. Thus, under designated assay conditions, the specified binding moieties bind preferentially to a particular target analyte and do not bind in a significant amount to other components present in a test sample. Specific binding to a target analyte under such conditions may require a binding moiety that is selected for its specificity for a particular target analyte. A variety of immunoassay formats may be used to select antibodies specifically immunoreactive with a particular protein. For example, solid-phase ELISA immunoassays are routinely used to select monoclonal antibodies specifically immunoreactive with an analyte. See Harlow and Lane (1988) *Antibodies, A Laboratory Manual*, Cold Spring Harbor Publications, New York, for a description of immunoassay formats and conditions that can be used to determine specific immunoreactivity. Typically a specific or selective reaction will be at least twice background signal or noise and more typically more than 10 to 100 times background.

Description of the Preferred Embodiments

This invention provides methods, compositions and kits for concentrating a target analyte from a sample. The methods involve the use of magnetic beads to concentrate the target analyte from the sample (see FIG. 1). In summary, these assays are performed by adding a target analyte binding moiety to a sample that contains, or is suspected of containing, the target analyte. The target analyte binding moiety and associated target analyte are concentrated by means of a magnetic bead to which is attached a capture moiety that is capable of reversibly binding to the target analyte binding moiety. After the magnetic bead/target analyte binding moiety/target analyte complex is formed, the complex is collected by application of a magnetic field to the sample. Finally, the target analyte binding moiety and associated target analyte are dissociated from the capture moiety under conditions that do not disrupt the capability of the target analyte binding moiety to bind to the target analyte, thus facilitating subsequent detection of the target analyte.

The use of a target analyte binding moiety and corresponding capture moiety that bind in a reversible manner provides significant advantages over previously known magnetic particle mediated purification methods. In earlier methods, the concentrated target analyte is typically detected while in the presence of the magnetic beads that were used to concentrate the target analyte. The sensitivity of detection assays was thus limited by nonspecific binding to the magnetic beads. As a sufficient number of beads were added to a sample to bind all or most of the analyte in the sample, the nonspecific binding to the beads increased, thus decreasing sensitivity. If fewer beads were used to decrease nonspecific binding, the sensitivity would also decrease because less than substantially all of the target analyte would be captured. Thus, the signal to noise ratio of these assays was relatively constant, placing a limit on sensitivity. This problem is particularly acute in situations where the target analyte is present in the sample in very dilute amounts and when large sample volumes are required to achieve the desired sensitivity.

The present invention solves this sensitivity problem by providing for dissociation of the target analyte binding complex and associated target analyte from the magnetic bead prior to the detection step. Because the magnetic beads can be removed prior to detection, nonspecific binding due to the beads is reduced or eliminated. The increase in the signal to noise ratio obtained using the claimed methods provides much greater sensitivity than was previously obtainable using magnetic separation methods. Therefore, a greater amount of beads can be used in the concentration step, ensuring that essentially all of the target analyte present in a relatively large sample volume is captured. For example, one can increase the amount of magnetic beads used by 100-fold or more compared to magnetic particle-based microtiter assays that were previously known. The assays for target analyte provided by the invention are highly sensitive, being able to detect levels of target analyte in a sample as low as 1 ng/ml. Preferably, the assay is able to detect 0.1 ng/ml or less target analyte, and most preferably the sensitivity is greater than about 0.01 ng/ml target analyte.

The methods of the invention use a target analyte binding moiety that is capable of specifically binding to the target analyte. A target analyte binding moiety can be, for example, a polypeptide such as an antibody, or an antibody fragment, that recognizes the particular target analyte of interest. Various procedures known in the art can be used for the production of antibodies that specifically bind to a particular target analyte. For the production of polyclonal antibodies, one can use the target analyte to inoculate any of various host animals, including but not limited to rabbits, mice, rats, sheep, goats, and the like. Polyclonal and monoclonal antibodies can also be prepared using recombinant techniques. Monoclonal antibodies can be prepared by any technique that provides for the production of antibody molecules by continuous cell lines in culture, including the hybridoma technique originally developed by Kohler and Milstein ((1975) *Nature* 256: 495–497), as well as the trioma technique, the human B-cell hybridoma technique (Kozbor et al. (1983) *Immunology Today* 4: 72), and the EBV-hybridoma technique to produce human monoclonal antibodies (Cole et al. (1985) in *Monoclonal Antibodies and Cancer Therapy*, Alan R. Liss, Inc., pp. 77–96). Monoclonal antibodies also can be produced in germ-free animals as was described in PCT/US89/02545 (Publication No. WO8912690, published Dec. 12, 1989) and U.S. Pat. No. 5,091,512. Other target analyte binding moieties include naturally occurring ligands that are specific for the target analyte; such ligands can be identified, for example, by affinity chromatography using immobilized target analyte as the affinity reagent. Non-naturally ocurring ligands, including those prepared using methods such as phage display, are also suitable for use as a target analyte binding moiety.

Preferably, the target analyte binding moiety is added to the sample in a sufficient amount and incubated with the sample for a time sufficient for substantially all target analyte in the sample to become associated with the target analyte binding moiety. For example, to 1 ml of a sample, which can be undiluted or diluted (e.g., 1–50 fold or greater dilution), one could add about 0.1 to about 5 µg of target analyte binding moiety and incubate for 10 min to 24 hr to obtain nearly complete association of target analyte with the binding moiety. Typically, the time required for binding substantially all of the target analyte decreases as the amount of target analyte binding moiety present in the sample increases.

To concentrate the target analyte/target analyte binding moiety complexes, a magnetic bead to which is attached a capture moiety that specifically binds to the target analyte binding moiety is added to the sample. Magnetic beads or particles, such as magnetic latex beads and iron oxide particles, that are useful in the claimed invention are known to those of skill in the art. For example, magnetic particles are described in U.S. Pat. No. 4,672,040. Magnetic particles are commercially available from, for example, PerSeptive Biosystems, Inc. (Framingham Mass.), Ciba Coming (Medfield Mass.), Bangs Laboratories (Carmel Ind.), and BioQuest, Inc. (Atkinson N.H.). Coupling of capture moieties to magnetic beads can be accomplished using known methods. For example, beads are commercially available that are derivatized with amino or carboxyl groups that are available for linkage to a protein or other capture moiety using, for example, glutaraldehyde, carbodiimide, diazoto compounds, or other suitable crosslinking reagent. Silanization of magnetically responsive particles provides one method of obtaining reactive groups on the surface of the particles (see, e.g., U.S. Pat. No. 4,672,040 for a description of silanization and silane coupling chemistry). Linking bonds can include, for example, amide, ester, ether, sulfonalmide, disulfide, azo, and others known to those of skill in the art. In one embodiment, the magnetic beads are iron oxide particles that are silanized. An example of suitable silanized beads having functional groups appropriate for covalent linking of capture moieties is the BioMag™ particle that is commercially available from PerSeptive Biosystems, Inc. Although covalent linkage of the anchor moiety to the magnetic bead is generally preferred, noncovalent linkages are also useful in the claimed methods and kits. For example, capture moieties can be attached to magnetic latex beads through non-covalent physical adsorption.

The capture moiety is capable of specifically binding, in a reversible manner, to the target analyte binding moiety. The capture moiety can bind to the target analyte binding moiety directly, or reversible binding between the capture moiety and the target analyte binding moiety can be achieved by attaching to the target analyte binding moiety a molecular tag that is chosen for its ability to specifically and reversibly bind to the capture moiety. Preferably, the binding of the capture moiety to the molecular tag is reversible under relatively mild conditions. The dissociation conditions are preferably sufficiently mild for the target analyte binding moiety and the target analyte to remain in contact with each other during and after the dissociation step and separation of magnetic beads, so that the target analyte binding moiety and target analyte immediately reassociate upon modification of the solution by, for example, neutralization. More preferably, the target analyte and target analyte binding moiety remain associated throughout the dissociation and separation steps. By maintaining or immediately reestablishing the association between the target analyte and its binding moiety, the resulting highly concentrated solution containing complexes of target analyte and the target analyte binding moiety can be applied directly to an assay device.

A molecular tag is preferably attached to the target analyte binding moiety by covalent bonding. For example, one method of obtaining a target analyte binding moiety that includes a molecular tag is to use a heterobifunctional linker to link the target analyte binding moiety to the molecular tag. Suitable linkers are known to those of skill in the art. One example of a suitable linker is the heterobifunctional linker SMCC (succinimidyl 4-[N-maleimidomethyl] cyclohexane-1-carboxylate; Sigma Chemical Co., St. Louis, Mo.), which can form a link between a amino residue (for example, lysine) and a thiol (such as that provided by cysteine). Other cross-linkers include, for example, m-maleimidobenzyl-N-hydroxysuccinimide ester (MBS) (Liu et al. (1979) *Biochemistry* 18: 690; Green et al. (1982) *Cell* 28: 477), glutaraldehyde, a carbodiimide succinyl anhydride, N-succinimidyl-3-[2-pyridyldithio]-propionate, and the like.

An additional method by which one can obtain a target analyte binding moiety that includes a peptide molecular tag is to construct a fusion gene in which a nucleic acid that codes for the binding component is operably linked to a nucleic acid that codes for the molecular tag. The nucleic acid encoding the molecular tag is preferably placed at a location in the binding component gene that does not disrupt the ability of the fusion protein obtained to bind to the target analyte. Where the binding component is an antibody, the molecular tag-encoding nucleic acid can be placed at or near the region of the antibody gene that encodes the carboxyl terminus of either the light chain or the heavy chain, or both. Methods for constructing and expressing genes that encode fusion proteins are well known to those of skill in the art. Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, N.Y., (Sambrook et al.); *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017,478; and Carr, European Patent No. 0,246,864.

Figure 2:
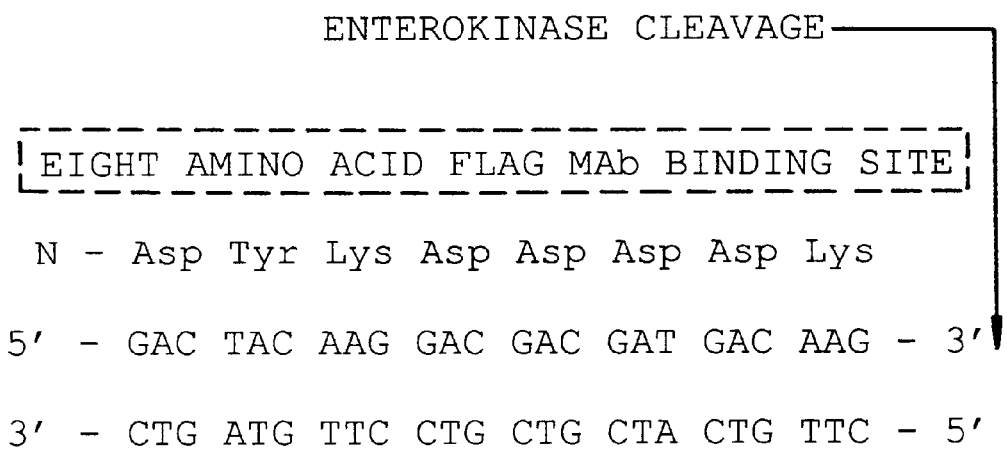
FIG. 2 shows the amino acid sequence of a FLAG peptide marker, and a nucleotide sequence that codes for this peptide. Also shown is a cleavage site for an enterokinase.

One example of a suitable molecular tag/capture moiety pair is the FLAG™ system (Kodak). The FLAG™ molecular tag consists of an eight amino acid FLAG peptide marker that is linked to the target analyte binding moiety. Conveniently, a target analyte binding moiety having a FLAG™ molecular tag is synthesized by cloning a 24 base pair FLAG coding sequence adjacent to a nucleotide sequence that codes for the target analyte binding moiety and expressing the fusion gene in an appropriate expression vector. The FLAG peptide marker (FIG. 2) also includes an enterokinase recognition site that corresponds to the carboxy-terminal five amino acids. Capture moieties suitable for use with the FLAG peptide marker include antibodies that bind to the FLAG™ peptide. For example, the Anti-FLAG M1, M2 and M5 monoclonal antibodies are commercially available. All eight amino acids of the FLAG peptide marker are required for binding of some anti-FLAG monoclonal antibodies; other antibodies may require fewer amino acids.

These anti-FLAG monoclonal antibodies differ in their preference for the location of the FLAG marker peptide relative to the protein it is fused to and in their ability to be bound to or released from the FLAG marker peptide in the presence or absence of calcium. The anti-FLAG M1 (IgG2b) monoclonal antibody binds to the FLAG epitope in the presence of calcium and requires a free amino group on the N-terminal aspartate for high affinity binding. Only the first four amino acids of the FLAG sequence (N-AspTyrLysAsp-C) are required for anti-FLAG M1 antibody binding; the presence of a glutamate at the fifth position (AspTyrLysAspGlu) increases the sensitivity by six-fold (Knappik and Pluckthun (1994) Biotechniques 17: 754–761). The anti-FLAG M1 monoclonal antibody is therefore useful as a capture moiety for binding FLAG peptides that are present on the amino terminus of the target analyte binding moiety. One advantage of the anti-FLAG M1 monoclonal antibody as a capture moiety is that because its binding to a FLAG epitope is calcium-dependent, one can the capture moiety from the target analyte binding moiety under extremely mild conditions such as by the addition of a chelating agent such as EDTA. Alternatively, dissociation can be accomplished by competition with FLAG peptide.

The anti-FLAG M5 (IgG1) monoclonal antibody has a high relative affinity for N-terminal Met-FLAG fusion proteins. N-terminal Met-FLAG fusion proteins are created by placing an ATG translational start codon immediately before the FLAG coding sequence. When transfected into an appropriate host, the N-terminal Met-FLAG fusion protein will be expressed in the cytoplasm of the cell. Unlike the anti-FLAG M1 monoclonal antibody, the binding of the anti-FLAG M5 antibody to the FLAG marker peptide is not calcium dependent. Where the target analyte binding moiety is an antibody that includes a FLAG molecular tag, a preferred capture moiety is the anti-FLAG M2 (IgG1) monoclonal antibody, which is also commercially available. This monoclonal antibody binds to the FLAG epitope regardless of its position relative to the remainder of the target analyte binding moiety. Therefore, the FLAG molecular tag can be placed in or near the carboxy terminus of the target binding antibody, thus avoiding disruption of the target analyte binding region. The binding of the anti-FLAG M2 monoclonal antibody is not calcium-dependent, but mild elution of FLAG fusion proteins from anti-FLAG M2 affinity columns can be accomplished by competition with FLAG peptide.

Another example of a suitable molecular tag is a polyhistidine sequence, which is capable of binding to metal chelate affinity ligands. Generally, at least two histidine residues are required to obtain binding to the ligand; the use of additional adjacent histidines increases the binding affinity. Typically, six adjacent histidines are used, although one can use more or less than six. Suitable metal chelate affinity ligands that can serve as the capture moiety for a polyhistidine molecular tag include nitrilo-tri-acetic acid (NTA) (Hochuli, E. (1990) "Purification of recombinant proteins with metal chelating adsorbents" In Genetic Engineering: Principles and Methods, J. K. Setlow, Ed., Plenum Press, N.Y.; commercially available from Qiagen (Santa Clarita, Calif.)). Dissociation of polyhistidine sequences from metal chelate affinity ligands can be achieved by bringing the solution containing the magnetic bead-bound complex to a mildly acidic pH such as, for example, pH 4. Also, one can dissociate binding by adding to the solution a chelating agent that competes with the molecular tag for binding to the capture moiety. Preferably, the competing chelating agent will have a higher affinity for the capture moiety than does the molecular tag associated with the target analyte binding moiety. Suitable chelating agents include imidazole. Other suitable metal chelate affinity ligands and corresponding methods for dissociation are known to those of skill in the art.

The decapeptide sequence YPYDVPDYAS and the hybridoma-derived antibody 7F11 are another suitable molecular tag/capture moiety pair. The decapeptide sequence can be attached to the target analyte binding moiety by, for example, attaching a thiol ester to one end of the peptide and attaching the peptide to the target analyte binding moiety by using a suitable heterobifunctional linker such as SMCC. Alternatively, a fusion gene can be constructed in which the reading frames for the decapeptide sequence and the target analyte binding moiety are operably linked. The antibody 7F11, which is a hybridoma-derived monoclonal antibody (deposited under the Budapest Treaty with the American Type Culture Collection (10801 University Boulevard, Manassas, Va. 20110-2209) on Dec. 5, 1997 and assigned ATCC Accession No. HB-12442) specifically binds to the decapeptide sequence and can be dissociated at pH 10.5 and higher.

To obtain other suitable molecular tag/capture moiety pairs for which binding is reversible under mild conditions, one can screen for peptides that bind a given molecular tag by, for example, enrichment of display libraries, including phage display libraries. A particularly useful method by which to obtain such reversibly binding molecular tag/capture moiety pairs is described in commonly owned U.S. patent application Ser. No. 08/832,985, filed Apr. 4, 1997, now U.S. Pat. No. 6,057,098. This method involves enriching conventional display libraries for members displaying more than one copy of a display polypeptide prior to affinity screening of such libraries with a target of interest, such as a molecular tag. The rationale for this method is believed to be that affinity binding of library members to an immobilized target occurs predominantly or exclusively through formation of multivalent bonds between multiple copies of displayed polypeptides on a library member and immobilized target. Accordingly, only members of library displaying multiple copies of a polypeptide are capable of binding to an immobilized target of interest. Conventional libraries typically have a distribution of number of polypeptides per member, in which most members display no copies of a polypeptide, a small proportion display one copy of a polypeptide, a still smaller proportion display two copies, and a still smaller proportion display three or more copies. The methods described in U.S. Pat. No. 6,057,098 enrich for the small proportion of conventional display libraries displaying two or more copies of a polypeptide. It is this rare fraction of conventional libraries that is capable of specific binding to an immobilized target.

Enrichment can be achieved by the inclusion of a marker as a component of the fusion protein from which polypeptides are displayed. The marker can be any polypeptide with a known receptor showing high binding specificity for the marker. The same marker is included in each member of the library. Enrichment is effected by screening the library for affinity binding to an immobilized receptor for the marker. Only library members having two copies of the marker are capable of binding to the immobilized receptor. By implication, library members having two copies of the marker have two copies of the fusion protein containing the marker, and two copies of a polypeptide to be screened. The library members that bind to the receptor thus constitute the small subpopulation of library members displaying two or more polypeptides. The library members not binding to the receptor are the majority of library members which display fewer than two copies of a polypeptide (i.e., zero or one copy). These library members, which would nonspecifically bind to the immobilized target in subsequent steps without contributing any members capable of specific binding, can thus be substantially eliminated.

After dissociation of the bound library members from the marker-specific receptor, these enriched library members, which display multiple copies of polypeptide, can then be subjected to one or more rounds of affinity screening to any immobilized target of interest. Because most library members that would otherwise contribute to nonspecific binding have been eliminated before affinity screening to the target, each round of affinity screening typically results in a greater enrichment for library members with affinity for the target than would be the case in conventional methods. The greater degree of enrichment per round of screening allows adequate screening to be accomplished in fewer rounds and/or a greater proportion of the repertoire of specifically binding library members to be identified.

So efficient are these selection methods that they result in diverse populations in which the vast majority of members retaining full-length coding sequences encode polypeptides having specific affinity for the target of interest, such as the molecular tag. These polypeptides may differ in fine binding specificity within the target and binding affinity for the target. Thus, one can use these methods to identify polypeptides that bind to the target in a manner that is reversible under mild conditions. This procedure involves the use of the target of interest as the affinity reagent. Binding is allowed to proceed to equilibrium and then the target is brought out of solution by contacting with a solid phase in a process known as panning (Parmley & Smith, *Gene* 73, 305–318 (1988)). Library members that remain bound to the solid phase do so by virtue of polyvalent bonds between them and target molecules. Unbound library members are washed away from the solid phase. Bound members are then dissociated from the solid phase (e.g., by change of ionic strength or pH). Members that are dissociated under relatively mild conditions such as, for example, a change in ionic strength or pH, or addition of a substance that competes with the tag for binding to the receptor, are then collected and used as capture moieties. For example, binding of metal chelate ligands immobilized on agarose and containing $Ni^{2+}$ to a hexahistidine sequence is easily reversed by adding imidazole to the solution to compete for binding of the metal chelate ligand. Antibody-peptide binding can often be dissociated by raising the pH to 10.5 or higher.

The dissociated library members are now enriched for two features: multivalent display of polypeptides and display of polypeptides having specific affinity for the target of interest. These library members can be subjected to further round(s) of affinity screening to the target without amplification. Alternatively, the library members can be amplified (e.g., by reinfection of bacteria and harvesting of progeny for a phage display library) to produce a secondary library. The secondary library remains enriched for display of polypeptides having specific affinity for the target, but, as a result of amplification, is no longer enriched for polyvalent display of polypeptides. Thus, a second cycle of polyvalent enrichment can then be performed, followed by a second cycle of affinity enrichment to the screening target. Further cycles of affinity enrichment to the screening target, optionally, alternating with amplification and enrichment for polyvalent display can then be performed, until a desired degree of enrichment has been performed.

The library members can also be used to obtain polyclonal capture moieties. The use of polyclonals has a number of advantages with respect to monoclonals. By binding to multiple sites on a target, polyclonal antibodies or other polypeptides can generate a stronger signal (for diagnostics) or greater blocking/inhibition/cytotoxicity (for therapeutics) than a monoclonal that binds to a single site. Further, a polyclonal preparation can bind to numerous variants of a prototypical target sequence (e.g., allelic variants, species variants, strain variants, drug-induced escape variants) whereas a monoclonal antibody may bind only to the prototypical sequence or a narrower range of variants thereto. Methods for obtaining polyclonals are described in commonly assigned U.S. patent application Ser. No. 08/832, 985, filed Apr. 4, 1997, now U.S. Pat. No. 6,057,098. In these methods, the nucleic acid sequences encoding displayed polypeptides such as are produced by the above methods can be subcloned directly into an expression vector without clonal isolation and testing of individual members. Generally, the sequence encoding the outer surface protein of the display vector fused to displayed polypeptides is not excised or amplified in this process. Once expressed in a suitable host cell, collections of antibodies or other polypeptides are purified from culture media and host cells. Usually, polypeptides are expressed with signal sequences and are thus released to the culture media. However, if polypeptides are not naturally secreted by host cells, the polypeptides can be released by treatment with mild detergent. Polypeptides can then be purified by conventional methods including ammonium sulfate precipitation, affinity chromatography to immobilized target, column chromatography, gel electrophoresis and the like (see generally Scopes, *Protein Purification* (Springer-Verlag, N.Y., 1982). These polypeptides can then be linked to magnetic beads as described below.

Other moieties are known that reversibly and specifically bind to an agent that is useful as a capture moiety. For example, certain derivatives of biotin such as 2-iminobiotin are available that bind to avidin in a pH-sensitive manner. Orr, G. (1981) *J. Biol. Chem.* 256: 761–766; commercially available from Pierce Chemical Co., Rockford Ill. This biotin derivative can be attached to the target analyte binding moiety as a molecular tag, while avidin is attached to the magnetic bead and serves as the capture moiety. To bind the target analyte binding moiety to the capture moiety, the sample and components are incubated at a pH of at least about 9, typically between pH 9–11, at which pH avidin strongly interacts with 2-iminobiotin. After concentration using a magnetic field, the target analyte binding moiety and bound target analyte are dissociated from the magnetic bead by adjusting the pH to about 6 or less and/or by adding biotin to the sample. Other examples of suitable molecular tags are known in the art.

To facilitate detection of target analyte after concentration using the described method, the target analyte binding moiety will also generally include a hapten or other group to which a detection moiety is capable of binding. The molecular tag can serve this function, or the target analyte binding moiety can be linked to a separate group, preferably by a covalent linkage. Suitable haptens are known to those of skill in the art and are described, for example, in the *Handbook of Fluorescent Probes and Research Chemicals* ($6^{th}$ Ed., Molecular Probes, Inc., Eugene Oreg.). For example, dinitrophenol (DNP), digoxigenin, barbiturates (see, e.g., U.S. Pat. No. 5,414,085), and several types of fluorophores are useful as haptens, as are derivatives of these compounds. Haptens are used in conjunction with a detection moiety that includes an antibody or other moiety that specifically binds to the particular hapten. Other groups that are useful for binding of the detection moiety include biotin, which is bound by a detection moiety that comprises avidin. Kits are commercially available for linking haptens and other moieties to proteins and other molecules. The molecular tag and hapten can be attached to the target analyte binding moiety simultaneously in the same reaction mixture.

For example, where both the molecular tag and the hapten include a thiol, a heterobifunctional linker such as SMCC can be used to attach the molecular tag and the hapten to lysine residues present on the target analyte binding moiety. Preferably, the target analyte binding moiety will include multiple molecular tags and haptens. By choosing the ratio of hapten to molecular tag present in an attachment reaction, one can control the ratio of hapten to molecular tag present on the target analyte binding moiety. Typically, the number of haptens attached to a target analyte binding moiety will be greater than the number of molecular tags; for example, suitable ratios of hapten: molecular tag include 2:1, 5:3, and the like.

The target analyte can be detected using detection moieties that are capable of specifically binding to the target analyte binding moiety, or to the target analyte itself. The detection moieties include at least a binding component and a detectable label. Suitable binding components include any moiety that is capable of specifically binding the target analyte or to the target analyte binding moiety. Antibodies and fragments thereof are examples of binding components that are suitable for use in detection moieties. The detection moieties will generally include, in addition to the binding moiety, a detectable label. Suitable detectable labels include any moiety that is detectable by spectroscopic, photochemical, biochemical, immunochemical, electrical, optical, chemical, or other means. For example, suitable labels include biotin for staining with labeled streptavidin conjugate, fluorescent dyes (e.g., fluorescein, Texas red, rhodamine, green fluorescent protein, and the like), radiolabels (e.g., $^3H$, $^{125}I$, $^{35}S$, $^{14}C$, or $^{32}P$), enzymes (e.g., horseradish peroxidase, alkaline phosphatase and others commonly used in an ELISA), and colorimetric labels such as colloidal gold or colored glass or plastic (e.g., polystyrene, polypropylene, latex, etc.) beads. Patents that described the use of such labels include U.S. Pat. Nos. 3,817,837; 3,850,752; 3,939,350; 3,996,345; 4,277,437; 4,275,149; and 4,366,241. See also *Handbook of Fluorescent Probes and Research Chemicals* ($6^{th}$ Ed., Molecular Probes, Inc., Eugene Oreg.). Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label. For use of the present invention in the clinic, and for other uses, preferred labels are non-radioactive and readily detected without the necessity of sophisticated instrumentation. Preferably, detection of the labels will yield a visible signal that is immediately discernable upon visual inspection.

The magnetic bead and associated capture moiety can be added to the sample before, after, or simultaneously with the target analyte binding moiety. Preferably, the magnetic beads are added to the sample in an amount and for a length of time sufficient for substantially all of the target analyte binding moiety, and associated target analyte, to become bound to the capture moiety. For example, to a 40 ml sample that was either undiluted or diluted 1–50-fold or more, one could add between 1 mg and 20 mg of magnetic beads. In a preferred embodiment, about 400 $\mu l$ of BioMag (1% solids) is used. The amount of beads added is inversely proportional to the time required to obtain substantially complete association of the target analyte binding moiety with the capture moiety.

After the target analyte binding moiety, target analyte, and the capture moiety have become associated into a magnetic bead-bound complex, a magnetic field is applied to the sample to collect the magnetic bead-bound complex. For example, the container containing the sample can be placed in the presence of a pole face of a permanent magnet, thus drawing the magnetic bead-bound complexes to an inner surface of the container. The unbound portion of the sample can then be removed by, for example, aspiration or by pouring from the container while the container remains in the presence of the magnetic field. Optionally, the magnetic bead-bound target analyte complex can then be washed, after which the container is returned to the magnetic field for re-collection of the magnetic bead-bound complex.

Following concentration of the magnetic bead-bound complex, the target analyte binding moiety and target analyte are generally dissociated from the magnetic bead and capture moiety. Dissociation conditions are chosen as is appropriate for the particular target analyte binding moiety and corresponding capture moiety used in the method. The magnetic beads can then be separated from the concentrated target analyte solution. If desired, the concentrated target analyte solution can be modified to facilitate detection. For example, if the pH of the solution was increased in order to effect dissociation of the magnetic beads from the target analyte binding moiety, after separation of the beads the solution can be modified by neutralization.

The methods, compositions and kits provided by the invention are useful for concentrating a wide variety of target analytes. Basically, any target analyte for which a ligand exists that is capable of binding to the target analyte, in a reasonably specific manner, can be concentrated using the described methods. For example, the methods are useful for concentrating haptens, hormones, peptides, proteins, drugs, and other substances of natural or synthetic origin. The target analytes can be free in the sample, or can be attached to a moiety such as a cell, in which case the invention provides a method for purifying a cell as a target analyte. For example, the methods are useful for concentrating bacterial organisms, including all enteric pathogens, These include, but are not limited to, *E. coli* (e.g., O157:H7), *Salmonella, Shigella, Helicobacter* (including *pylori*), *Campylobacter* (including *jejuni* and *coli*). To obtain target analyte binding moieties that are capable of specifically binding to these bacterial strains, antibodies can be raised against outer membrane proteins, for example, by using an outer membrane preparation from the bacterial species of interest as an immunogen in classical immunological methods. Alternatively, phage display can be used to identify binding moieties that bind to outer membrane proteins. Target analyte binding moieties for use in concentrating cells are best prepared using outer membrane preparations, as opposed to isolated outer membrane proteins, because antibodies raised against the latter often recognize an epitope that is not exposed when the protein is present in the membrane of an intact cell.

Figure 4A:
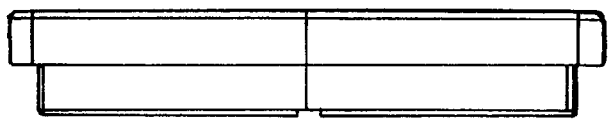
FIGS. 4A–4C shows a bottom piece of an apparatus for performing an immunoassay for detection of a target analyte.
Figure 4B:
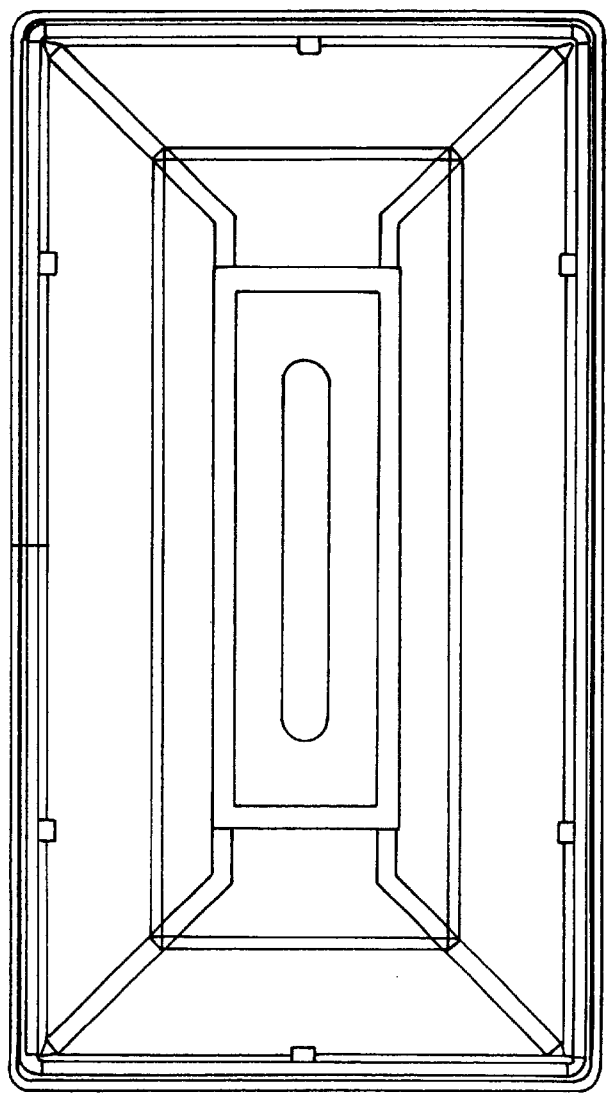
Figure 4C:
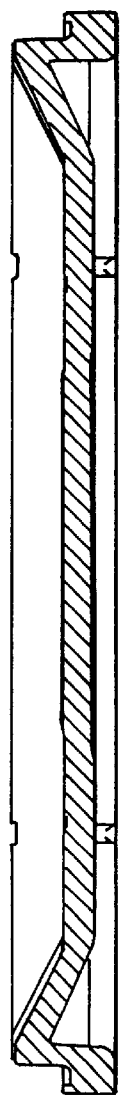

In one highly sensitive and specific assay provided by the invention, bacterial cells are concentrated using a target analyte binding moiety that is specific for an outer membrane protein. The concentration step is highly specific because outer membrane proteins are generally unique to each particular bacterial species. Once the bacteria of interest in a sample have been concentrated, a detection moiety is used that is capable of specifically binding to the bacterial lipopolysaccharide (LPS). LPS is much more abundant than is outer membrane protein, resulting in a large amplification factor. For the greatest sensitivity, the bacterial cells are disrupted after concentration to expose more LPS to the detection moiety. In addition to, or instead of, disruption, the cells can be placed on an assay device such as that shown in FIGS. 3 and 4. In one example of this assay, monoclonal antibodies specific for outer membrane proteins of Salmonella (Kerr et al. (1992) *J. Appl. Bacteriol.* 72: 302) are selected for use as the target analyte binding moiety. After the Salmonella present in the sample are dissociated and separated from the magnetic particles of the invention, the Salmonella with antibodies attached to outer membrane proteins are detected using a sandwich assay. Suitable detection moieties include monoclonal antibodies to outer core polysaccharides of Salmonella LPS that have been developed and which bind to all Salmonella species (Tsang et al. (1987) *Infect. Immun.* 55: 211; Luk et al. (1991) *J. Biol. Chem.* 266: 23215).

In an alternative embodiment, anti-LPS antibodies are used as both anchor and detection moieties to sequentially capture the target bacteria on a solid phase and then detect the immobilized organisms through binding of the detection moiety to the remaining LPS not bound to the anchor moiety. Another embodiment uses antibodies specific for bacterial LPS as the target analyte binding moiety. The antibodies can be labeled as described herein with a molecular tag for capture by a capture moiety and with a hapten for detection using the detection moiety. Following dissociation of the bacteria from the magnetic particles, antibodies specific for the hapten can be used as both anchor and detection moieties in a sandwich assay to detect the presence of the bacterial cells. This and other variations of the assays provided by the invention for detecting bacteria are shown in Table 1.

TABLE 1

| Target Analyte Binding Moiety | Anchor Moiety | Detection Moiety |
|---|---|---|
| Anti-OMP | Anti-LPS | Anti-LPS |
| Anti-OMP labeled with a hapten | Anti-hapten | Anti-LPS |
| Anti-LPS | Anti-LPS | Anti-LPS |
| Anti-LPS labeled with a hapten | Anti-hapten | Anti-LPS |
| Anti-LPS or anti-OMP labeled with a hapten | Anti-LPS or anti-OMP | Anti-hapten |

The methods, compositions and kits provided by the invention are useful for concentrating a target analyte from a wide variety of test samples, including biological samples such as cultures, tissue samples bodily fluids, food products, environmental samples, and the like. For liquid or semi-solid biological samples, a portion of the sample is added to an assay container and, optionally, diluted with a suitable diluent such as water or an appropriate buffer and mixed. Suitable buffers include, for example, buffered protein solutions and the like. Solid samples can be placed in a diluent and suspended by vigorous mixing. Typically, the sample is diluted sufficiently to provide a solution of suitable clarity for use in the assays; this is generally about a 3–20 fold dilution, with about a 10-fold dilution being typical. After mixing, one can clarify the sample by, for example, filtration or centrifugation or other methods known to those of skill in the art. In general, well known methods for preparing test samples for assays, such as immunoassays, are suitable for preparing test samples for analysis using the methods provided by the claimed invention.

The reduction in nonspecific binding achieved by use of reversibly associating capture moieties and target analyte moieties makes possible the use of various methods to detect the presence of target analyte. One convenient format for clinical and other use involves an immunoassay. For example, after removing the magnetic beads from the solution containing the concentrated target analyte, the solution can be applied to a solid support upon which is immobilized an anchor moiety that specifically binds to an epitope of the target analyte. This epitope can be the same as or different than the target analyte epitope to which the target analyte binding moiety binds (see FIG. 1). Suitable supports include, for example, glasses, plastics, polymers, metals, metalloids, ceramics, organics, and the like. Specific examples include, but are not limited to, microtiter plates, nitrocellulose membranes, nylon membranes, and derivatized nylon membranes, and also particles, such as agarose, SEPHADEX™, and the like. To immobilize the target analyte on the solid support, an anchor moiety is non-diffusively associated with the support. The anchor moiety is capable of specifically binding to the target analyte. Antibodies that are specific for the target analyte, and fragments of such antibodies, are examples of anchor moieties that are suitable for use in the assays of the invention. The anchor moieties can be non-diffusively immobilized on the support either by covalent or non-covalent methods, which are known to those of skill in the art. See, e.g., Pluskal et al. (1986) *BioTechniques* 4: 272–283.

The assays can be performed in any of several formats. For example, a sandwich assay can be performed by preparing a sample as discussed above, or as is otherwise appropriate for the particular sample, and placing the sample in contact with a solid support to which is immobilized a plurality of anchor moieties for the target analyte which, if present in the sample, binds to the anchor moieties. The solid support can be washed to remove unbound reagents, if desired. A detection moiety that is specific for the target analyte or to the target analyte binding moiety is also applied to the solid support. After incubation of the detection moieties for a sufficient time to bind a substantial portion of the immobilized target analyte, any unbound labeled reagents are removed by, for example, washing. The presence or absence of the detectable label is then determined by methods appropriate for the particular label employed. For example, in the case of an enzyme used as a detectable label, a substrate for the enzyme that turns a visible color upon action of the enzyme is placed in contact with the bound detection moiety. A visible color will then be observed in proportion to the amount of the specific antigen in the sample.

In another embodiment, the detection moieties and/or one or more additional components necessary for detection can be added to the sample prior to, or simultaneously with, the contacting of the sample with the solid support. The target analyte (or target analyte binding moiety, depending on the particular detection moiety used) can then become associated with the detection moiety prior to becoming immobilized on the solid support. This can result in an assay that requires fewer manipulations by the clinician.

Assay systems for use in the methods and kits of the invention include, but are not limited to, dipstick-type devices, immunochromatographic test strips and radial partition immunoassay devices, and flow-through devices. Conveniently, where the solid support is a membrane, the sample will flow through the membrane, for example, by gravity, capillary action, or under positive or negative pressure. Preferred assay systems for use in the kits and methods of the invention are described in EP 447154. These systems employ an apparatus as shown in FIGS. 3A–3C and 4A–4C, which apparatus includes a porous member such as a membrane or a filter onto which is bound a multiplicity of anchor moieties for the target analyte.

The apparatus also includes a non-absorbent member with a textured surface in communication with the lower surface of the porous member. The textured surface of the non-absorbent member can be a grooved surface such as the surface of a record or it can be composed of channels, such that when the porous and non-absorbent members are brought into contact with one another a network of capillary channels is formed. The capillary network is formed from the contact of the porous member with the textured surface of the non-absorbent member and can be constructed either before or subsequent to the initial contacting of the porous member with a fluid. In some embodiments, the capillary communication between the porous member and the non-absorbent member favors delaying the transferral of fluid from the porous member to the capillary network formed by the porous member and the textured surface of the non-absorbent member until the volume of the added fluid substantially exceeds the void volume of the porous member. The transferral of fluid from the porous member to the network of capillary channels formed by the porous member and the textured surface of the non-absorbent member can occur without the use of external means, such as positive external pressure or vacuum, or contact with an absorbent material.

The devices of the present invention can also include an optional member which is placed in contact with the upper surface of the porous member and may be used to partition the upper surface of the device into discrete openings. Such openings can access either the porous member or the textured surface of the non-absorbent second member. The optional member can in conjunction with the non-absorbent member compose a fluid receiving zone in which there is no intervening porous member. A fluid receiving zone constructed from the non-absorbent member and the optional member provides fluid capacity in addition to that provided by the network of capillary channels created by the contact of the porous member and the non-absorbent member. The openings in the optional member may include a first fluid opening and also an additional fluid opening. The first fluid opening functions as a portal for the introduction of the first fluid added to the device. The additional fluid opening serves as an additional portal through which additional fluids may be added to the inventive device.

To perform an assay using these devices, a volume of the sample is added to the porous member, where the sample permeates the void volume of the porous member and thereby contacts the anchor moieties immobilized on the porous member. In a non-competitive assay, the sample to be assayed is applied to the porous member and the target analyte, if present, is bound by the anchor moieties. Detection moieties for the target analyte are then added as an additional fluid; these bind to the complex of target analyte and anchor moiety. Alternatively, the detection moieties can be added to the sample prior to application of the sample to the porous member so that the binding of detection moiety to the target analyte occurs prior to binding of the target analyte to the anchor moiety. In another embodiment, the anchor moieties and detection moieties are added to the sample, after which the complex of anchor moiety, target analyte, and detection moiety binds to a binding agent that is either combined with these reagents or is immobilized on the porous member. An additional fluid containing reagents to effect a separation of free from bound labeled reagents can be added to remove excess detection moiety, if needed.

This device is designed to provide sufficient sensitivity to measure low concentrations target analyte because one can use large amounts of sample. Indeed, the efficient separation of free from bound label achieved by the network of capillary channels of this device improves the discrimination of specific target analyte-associated signal over non-specific background signal. If needed, a signal developer solution is then added to enable the label of the detection moiety to develop a detectable signal. The signal developed can then be related to the concentration of the target ligand within the sample. In a preferred embodiment, the transfer of fluid between the porous first member of the device and the network of capillary channels formed by the contact of the porous member and textured surface of the non-absorbent second member of the device is generally self-initiated at the point when the total volume of fluid added to the device exceeds the void volume of the porous member, thus obviating the need for active interaction by the user to remove excess fluid from the analyte detection zone. The point at which the fluid transfer is initiated is dependent upon the objectives of the assay. Normally, it is desirable to contact the sample with all of the zones on the porous member which contain immobilized receptor so that the application of additional fluid effects the separation of unbound label from label which has bound to the porous member. This method enables the detection of the target analyte in a manner that is simple, rapid, convenient, sensitive and efficient in the use of labeled reagents.

Competitive binding assays can also be used to detect a target analyte after its concentration using the magnetic bead purification. Conveniently, these assays are performed using the described devices by adding to a sample a labeled analog of the target analyte. The labeled analog and any target analyte present in the sample compete for the binding sites of the anchor moieties. Alternatively, the anchor moieties can be combined with the sample and labeled analogs with subsequent immobilization of the anchor moieties onto the porous member through contact with a binding agent. An additional fluid to separate the free from bound label may be added to the device, followed if needed by a signal development solution to enable detection of the label of the labeled analog which has complexed with anchor moiety immobilized on the porous member. The amount of labeled target analyte or analog bound to the porous member is related to the concentration of target analyte in the sample.

The invention also provides kits for detecting the presence of target analytes using magnetic beads as described herein. The kits can include a container that contains a target analyte binding moiety that is capable of specifically binding to a target analyte of interest, a magnetic bead to which is attached a capture moiety that specifically and reversibly binds to the target analyte binding moiety, a solid support upon which is immobilized an anchor moiety that specifically binds to at least one epitope of the target analyte. The epitope to which the anchor moiety binds can be the same as or different than the target analyte epitope to which the target analyte binding moiety binds. The kits can also include a detection moiety that is conjugated to a detectable label and specifically binds to the target analyte, to the target analyte binding moiety, or to a hapten present on the target analyte binding moiety. Preferably, the kits will also include reagents used in the described assays, including reagents useful for detecting the presence of the detectable label. Other materials useful in the performance of the assays can also be included in the kits, including test tubes, magnets, transfer pipettes, and the like. Kits can contain materials sufficient for one assay, or can contain sufficient materials for multiple assays, for example, materials for 10, 25, 50, or more assays can be provided in a single kit. The kits can also include instructions for the use of one or more of these reagents in any of the assays described herein.

The kits of the invention can also include appropriate controls to ensure that the assay is working correctly for a particular sample, and has the desired sensitivity. The control can be an amount of the target analyte of interest; this control antigen can conveniently be preattached to the anchor moiety in a zone adjacent to the zone to which the sample is applied. Typically, the control target analyte will be at a concentration at or above the sensitivity limit of the assay means. The control target analyte can be diluted in the sample diluent and assayed in the same manner as would a biological or other sample.

Alternatively, control target analyte can be added to an aliquot of an actual biological sample to determine the sensitivity of the assay.

The present invention also provides highly concentrated preparations that include a target analyte and a target analyte binding moiety. These preparations are prepared using the methods described above which involve reversible binding of the target analyte binding moiety to a capture moiety that is linked to a magnetic bead. The concentration of target analyte in the claimed concentrated preparations is typically at least about 2-fold greater than the target analyte concentration in the test sample from which the concentrated preparation was prepared. More preferably, the concentrated preparation will be at least about 10-fold more concentrated, and most preferably at least about 1000-fold more concentrated than the test sample.

EXAMPLE

The following example is offered to illustrate, but not to limit the present invention.

High-Sensitivity Assay for *C. difficile* Toxin A using Magnetic Beads

This assay used magnetic beads to concentrate *C. difficile* toxin A from a sample prior to detecting the toxin A by sandwich assay. A schematic of the assay strategy is shown in FIG. 1.

A. Preparation of Monoclonal Antibodies 7F11 and 3E12

1. Synthesis of Acetylthiopropionic Acid.

To a stirred solution of 3-mercaptopropionic acid (7 ml, 0.08 moles) and imidazole (5.4 g, 0.08 moles) in tetrahydrofuran (THF, 700 ml) was added dropwise over 15 minutes, under argon, a solution of 1-acetylimidazole (9.6 g, 0.087 moles) in THF (100 ml). The solution was allowed to stir a further 3 hours at room temperature after which time the THF was removed in vacuo. The residue was treated with ice-cold water (18 ml) and the resulting solution acidified with ice-cold concentrated HCl (14.5 ml) to pH 1.5–2. The mixture was extracted with water (2×50 ml), dried over magnesium sulfate and evaporated. The residual crude yellow oily solid product (10.5 g) was recrystallized from chloroform-hexane to afford 4.8 g (41% yield) acetylthiopropionic acid as a white solid with a melting point of 44–45° C.

2. Decapeptide and Barbiturate Derivatives

The decapeptide, YPYDVPDYAS, (Chiron Mimotopes Peptide Systems, San Diego, Calif.) was dissolved (0.3 g) in dry DMF (5.4 mL) in a round bottom flask under argon with moderate stirring. Imidazole (0.02 g) was added to the stirring solution. Separately, acetylthiopropionic acid (0.041 g) was dissolved in 0.55 mL of dry DMF in a round bottom flask with stirring and 0.056 g of 1,1'-carbonyldiimidazole (Aldrich Chemical Co., Milwaukee, Wis.) was added to the stirring solution. The flask was sealed under argon and stirred for at least 30 minutes at room temperature. This solution was added to the decapeptide solution and the reaction mixture was stirred for at least six hours at room temperature before the solvent was removed in vacuo. The residue in the flask was triturated twice using 10 mL of diethyl ether each time and the ether was decanted. Methylene chloride (20 mL) was added to the residue in the flask and the solid was scraped from the flask and filtered using a fine fritted Buchner funnel. The solid was washed with an additional 20 mL of methylene chloride and the Buchner funnel was dried under vacuum. In order to hydrolyze the derivative to generate a free thiol, it was dissolved in 70% DMF and 1 N potassium hydroxide was added to a final concentration of 0.2 N while mixing vigorously. The derivative solution was allowed to stand for 5 minutes at room temperature prior to neutralization of the solution by the addition of a solution containing 0.5 M potassium phosphate, 0.1 M borate, pH 7.0, to which concentrated hydrochloric acid has been added to a final concentration of 1 M. The thiol concentration of the hydrolyzed decapeptide derivative was determined by diluting 10 μL of the solution into 990 μL of a solution containing 0.25 mM 5,5'-dithiobis (2-nitrobenzoic acid) (DTNB, Aldrich Chemical Co., Milwaukee Wis.) and 0.2 M potassium borate, pH 8.0. The thiol concentration in mM units was equal to the $A_{412}(100/13.76)$. The barbiturate derivative was prepared as described in U.S. Pat. No. 5,414,085, Example 3.

3. Preparation of Conjugates of Barbiturate Derivative and Decapeptide Derivative with Keyhole Limpet Hemocyanin and Bovine Serum Albumin Keyhole limpet hemocyanin (KLH, 6 ml of 14 mg/ml, Calbiochem, San Diego, Calif.) was reacted with sulfosuccinimidyl 4-(N-maleimidomethyl)cyclohexane-1-carboxylate (SULFO-SMCC) by adding 15 mg of SULFO-SMCC and maintaining the pH between 7 and 7.5 with 1N potassium hydroxide over a period of one hour at room temperature while stirring. The protein was separated from the unreacted SULFO-SMCC by gel filtration chromatography in 0.1 M potassium phosphate, 0.02 M potassium borate, and 0.15 M sodium chloride, pH 7.0, and 24 ml of KLH-maleimide was collected at a concentration of 3.1 mg/ml. The hydrolyzed barbiturate derivative and the hydrolyzed decapeptide derivative were separately added to portions of the KLH-maleimide in substantial molar excess over the estimated maleimide amounts present and the solutions were stirred for 4 hours at 4° C. and then each was dialyzed against 3 volumes of one liter of pyrogen-free phosphate-buffered saline, pH7.4. prior to immunization.

Bovine serum albumin (BSA, 3.5 ml of 20 mg/ml) was reacted with SMCC by adding a solution of 6.7 mg of SMCC in 0.3 ml acetonitrile and stirring the solution for one hour at room temperature while maintaining the pH between 7 and 7.5 with 1N potassium hydroxide. The protein was separated from unreacted materials by gel filtration chromatography in 0.1 M potassium phosphate, 0.02 M potassium borate, 0.15 M sodium chloride, pH 7.0. The hydrolyzed barbiturate derivative and the hydrolyzed decapeptide derivative were separately added to portions of the BSA-maleimide in substantial molar excess over the estimated maleimide amounts present and the solutions were stirred for 4 hours at 4° C. The solutions were used to coat microtiter plates for the detection of antibodies 10 that bound to either the barbiturate derivative or the decapeptide derivative by standard techniques.

4. Production of Hybridomas and Primary Selection of Monoclonal Antibodies

Immunization of Balb/c mice was performed according to the method of Liu, D., Purssell, R., and Levy, J. G., Clin.

Chem., 25: 527–538 (1987). Fusions of spleen cells with SP2/0-Ag 14 myeloma cells, propagation of hybridomas, and cloning were performed by standard techniques. Selection of hybridomas for further cloning began with culture supernatant at the 96-well stage. A standard ELISA procedure was performed with BSA conjugates of either barbiturate derivative or decapeptide derivative adsorbed to the ELISA plate. Typically, a single fusion was plated out in twenty plates and approximately 10–20 wells per plate were positive by the ELISA assay. At this stage, a secondary selection could be performed if antibodies to the SMCC part of the linking arm were to be eliminated from further consideration. An ELISA assay using BSA derivatized with SMCC but not linked to either derivative identified which of the positive clones that bound the BSA conjugates were actually binding the SMCC-BSA. The antibodies specific for SMCC-BSA may be eliminated at this step. Monoclonal antibodies 7F11, specific for the decapeptide derivative, and 3E12, specific for the barbiturate derivative, were produced and selected by this process. Cells that produce each of these antibodies have been deposited under the Budapest Treaty with the American Type Culture Collection (12301 Parklawn Drive, Rockville Md. 20852) on Dec. 5, 1997, and have been assigned ATCC Accession Nos. HB-12442 (3E12) and HB-12443 (7F11).

B. Preparation of Detection Moiety

The recombinant antibody 3E12 was used to construct the detection moiety. This antibody, which binds specifically to a barbiturate derivative that was attached to the toxin A binding moiety as a hapten, was conjugated to alkaline phosphatase. Intact IgG antibody 3E12 was reacted with succinimidyl 3-(2-pyrridyldithio)propionate (SPDP, Molecular Probes, Eugene, Oreg.) using antibody at 10 mg/ml and a ratio of 10:1 SPDP:antibody in a buffer containing 50 mM potassium phosphate, 10 mM borate, 150 mM sodium chloride, pH 7.0, for 90 minutes at room temperature. The reaction was stopped by adding aminoethanesulfonic acid (Sigma Chemical Co., St. Louis, Mo.) to a final concentration of 20 mM. The reagent DTT was added to 2 mM final concentration and the reduction was allowed to proceed for 30 minutes at room temperature. The antibody was separated from the low molecular weight reactants by gel filtration chromatography using a column containing G50 Fine in the above buffer with 0.1 mM EDTA present.

Alkaline phosphatase (AP, Calzyme Laboratories, San Luis Obispo, Calif.) was dialyzed against a minimum of 100 volumes of column buffer (50 mM potassium phosphate, 10 mM borate, 150 mM NaCl, 1mM $MgSO_4$, pH 7.0) at 2–8° C. for a minimum of four hours and the buffer was changed at least twice prior to use of the AP. After the AP was removed from dialysis and brought to room temperature, the concentration was determined by determining the $A_{280}$, with an absorbance of 0.77 indicating a 1 mg/ml solution. The AP was diluted to 5 mg/ml with column buffer.

For crosslinking the AP to the antibody, AP was first linked to succinimidyl 4-(N-maleimidomethyl cyclohexane-1-carboxylate (SMCC, Pierce Chemical Co., Rockford Ill.) using a 20:1 ratio of SMCC:AP. SMCC was dissolved in acetonitrile at 20 mg/ml and diluted by a factor of 84 when added to AP while vortexing or rapidly stirring. The solution was allowed to stand at room temperature for 90 minutes before the unreacted SMCC and low molecular weight reaction products were separated from the AP using gel filtration chromatography (G50 Fine, Pharmacia Biotech. Piscataway, N.J.) in a column equilibrated with column buffer.

The AP and the derivatized antibody were mixed together in a molar ratio of 1:1 and the conjugation reaction was allowed to continue overnight at room temperature. To stop the conjugation, 2-mercaptoethanol was added to 1 mM final concentration to the conjugate solution and reacted for 5 minutes followed by the addition of N-ethyl maleimide to 2 mM final concentration. The conjugate was purified by gel filtration chromatography using SEPHACRYL™ S-500 HR (Pharmacia Biotech, Piscataway, N.J.). The free antibody was excluded from the conjugate pool which was diluted for use in immunoassays using the conjugate diluent described above.

C. Preparation of Capture Moiety

The monoclonal antibody 7F11, which specifically binds to the decapeptide sequence YPYDVPDYAS, was prepared as described above. To construct the capture moiety, the antibody 7F11 was coupled to magnetic particles as follows. Amine terminated BioMag™ particles (PerSeptive Biosystems, Framingham, Mass.) with a nominal size distribution of 2.5 μm were initially washed with deionized water. A volume of 52.6 ml of 3.8% particles was washed by magnetic separation from the storage solution followed by resuspension in deionized water and magnetic separation using permanent magnets obtained from PerSeptive Biosystems. The BioMag particles were resuspended in 188 ml of deionized water and 20 ml of 500 mM potassium phosphate, 100 mM borate, pH 7.0, was added and mixed. The crosslinking agent SMCC (124 mg) was dissolved in 20 ml of dry N,N-dimethylformamide (DMF, Aldrich Chemical Co., Milwaukee, Wis.) and the solution was added to the BioMag suspension. The reaction was allowed to proceed with gentle rocking for two hours at room temperature. To stop the reaction, 2-aminoethanesulfonic acid was added to a final concentration of 20 mM and reacted for 15 minutes at room temperature. The BioMag was washed five times using magnetic separation with five 200-ml volumes of 50 mM potassium phosphate, 10 mM borate, 10% DMF, pH 7.0. The SMCC-BioMag particles were resuspended in 100 ml of 50 mM potassium phosphate, 10 mM borate, 150 mM sodium chloride, 0.1 mM EDTA, pH 7.0.

The monoclonal antibody 7F11 was derivatized by diluting to 5 mg/ml and mixing 100 ml of this solution with 5.2 mg of SPDP that had been dissolved in 0.2 ml of acetonitrile. The reaction was allowed to proceed for 90 minutes at room temperature before 2-aminoethanesulfonic acid was added to a final concentration of 20 mM and reacted for 15 minutes. DTT was added to a final concentration of 2 mM and reacted for 30 minutes at room temperature. The antibody solution was concentrated to 20 ml using a YM 30 ultrafiltration membrane (Amicon, Beverly, Mass.) and the antibody was subjected to gel filtration chromatography using a column containing GH-25 (Amicon, Beverly, Mass.) in 50 mM potassium phosphate, 10 mM borate, 150 mM sodium chloride, 0.1 mM EDTA, pH 7.0. The antibody eluting from the column was collected and diluted to 100 ml with the same buffer.

The SPDP-derivatized antibody 7F11 was then mixed with the SMCC-BioMag particle suspension. The final antibody concentration was 2.3 mg/ml and the final particle concentration was 1% solids. The reaction proceeded for 18 hours at room temperature with gentle rocking before it was stopped by adding 2-mercaptoethanol to a final concentration of 2 mM followed by a 30-minute incubation and the addition of N-hydroxyethylmaleimide to a final concentration of 6 mM. The 7F11-BioMag was washed five times with five 200-ml volumes of 50 mM potassium phosphate, 10 mM borate, 150 mM sodium chloride, pH 7.0, using magnetic separation and the particles were stored at 1% solids in this buffer containing 0.1% sodium azide.

D. Preparation of Toxin A Binding Moiety The toxin A binding moiety was based on the monoclonal antibody PCG-4, which specifically binds to *C. difficile* toxin A and is described in U.S. Pat. No. 4,533,630. A barbiturate derivative was attached to the antibody as a hapten to bind the detection moiety, and a decapeptide sequence was attached to the antibody as a molecular tag to bind the capture moiety.

To attach the barbiturate derivative to monoclonal antibody PCG-4, the antibody was prepared at 10 mg/ml in 50 mM potassium phosphate, 10 mM borate, 150 mM sodium chloride, 0.1 mM EDTA, pH 7.0. SMCC was added to a final molar ratio of 25:1 SMCC: antibody using a solution of SMCC at 20 mg/ml in acetonitrile. The reaction was allowed to proceed for 90 minutes at room temperature prior to separation of the antibody from the SMCC by gel filtration chromatography in a column containing G50 Fine in the above buffer. The SMCC-PCG-4 was collected and the concentration determined by $A_{280}$ using an absorbance of 1.4 for a 1 mg/ml solution.

Barbiturate derivative was dissolved in 70% DMF and 1 N potassium hydroxide was added to a final concentration of 0.2 N while mixing vigorously. The derivative solution was allowed to stand for 5 minutes at room temperature prior to neutralization of the solution by the addition of a solution containing 0.5 M potassium phosphate, 0.1 M borate, pH 7.0, to which concentrated hydrochloric acid has been added to a concentration of 1 M. The thiol concentration of the hydrolyzed barbiturate derivative was determined by diluting 2 μL of the solution into 998 μL of a solution containing 0.25 mM 5,5'-dithiobis(2-nitrobenzoic acid) (DTNB, Aldrich Chemical Co., Milwaukee Wis.) and 0.2 M potassium borate, pH 8.0. The thiol concentration in mM units was equal to the $A_{412}$(500/13.76).

The decapeptide derivative was similarly prepared by hydrolysis and its thiol concentration was also determined.

The barbiturate and decapeptide derivatives were attached to the derivatized PCG-4 antibody as follows. The SMCC-PCG-4 preparation was typically at a concentration of 2–3 mg/ml. The hydrolyzed barbiturate and decapeptide derivatives were mixed together so that when added to the antibody solution, the final thiol concentration was 0.3 mM and the ratio of hydrolyzed barbiturate derivative to hydrolyzed decapeptide derivative was 2:1. The reaction was allowed to proceed for 30 minutes at room temperature before the barbiturate/decapeptide-PCG-4 antibody was placed into dialysis vs. one liter of BBS.

E. High Sensitivity Assay for Toxin A

The assay was carried out essentially as shown in FIG. 1. Barbiturate/decapeptide-PCG-4 antibody (toxin A binding moiety) was added to 7F11-BioMag (capture moiety) to a final concentration of approximately 50 μg/ml of 7F11-BioMag at 1% solids. The antibody was allowed to bind via the affinity of 7F11 for the decapeptide derivative for 5 minutes prior to washing the BioMag with one volume of dissociation buffer followed by one volume of neutralization buffer followed by three volumes of 50 mM potassium phosphate, 10 mM borate, 150 mM sodium chloride, pH 7.0, with final storage at 1% solids in this buffer.

Stool samples were taken in amounts of 5 grams or 5 ml and diluted to 40 ml with a sample diluent containing 10 mM potassium phosphate, 150 mM sodium chloride, 0.1% casein, 0.01% bovine IgG, 0.05% TRITON X-100™, pH 7.6. The diluted samples were filtered through glass wool to remove large debris and 400 μL of barbiturate/decapeptide-PCG-4-7F11-Biomag was added to the diluted sample in a 50-ml conical tube. The mixture was placed on a rocker to keep the BioMag suspended for 30–60 minutes at room temperature. The samples were then placed on a magnetic separation rack (Perseptive Biosystems, Framingham, Mass.) and the BioMag was allowed to separate from the sample for 5 minutes. The liquid was decanted from the sample container and discarded, the BioMag was resuspended in the sample diluent, and the sample container was placed back in the magnetic separation rack for another five minutes. The solution was decanted again and discarded.

To dissociate the binding of the capture moiety to the decapeptide sequence, the BioMag complex was resuspended in 300 μL of dissociation buffer containing 50 mM potassium phosphate, 150 mM NaCl, pH 11.5. The BioMag was incubated for two minutes in this solution before separation of the BioMag from the solution in the magnetic separation rack. The solution was removed and subjected to centrifugation for approximately 20,000 g min. The clarified solution was removed from the centrifuge tube and neutralized by adding 200 μL of a neutralization buffer containing 200 mM N-[2-hydroxyethyl]piperazine-N'-[3-propanesulfonic acid] (HEPPS, Calbiochem, La Jolla Calif.), 150 mM sodium chloride, 0.8% casein, 0.15 sodium azide, 50 μM decapeptide derivative that had been hydrolyzed and reacted with N-ethylmaleimide, pH 7.3.

The sample was then added to an immunoassay device as described above containing a line of immobilized polyclonal antibody specific for toxin A, CD.TXA.1.PC, conjugated to casein. Preparation of this antibody, which is a recombinant polyclonal antibody, is described in commonly assigned U.S. patent application Ser. No. 08/832,985, filed Apr. 4, 1997, now U.S. Pat. No. 6,057,098. The antibody was immobilized on the porous membrane of the assay device as described above, using a solution containing approximately 5 mg/ml of antibody. After the sample drained into the device, the conjugate of 3E12 and alkaline phosphatase was added in a volume of 140 μL at a concentration of approximately 20 μg/ml in the conjugate diluent described above and allowed to react for 3 minutes at room temperature.

After the incubation, five drops of wash solution containing 100 mM tris (hydroxymethyl) aminomethane (TRIS, Fisher Scientific, Pittsburgh, Pa.), 150 mM sodium chloride, 0.5% Dow 193 surfactant, 0.1% sodium azide, and 20 mg/L of NBT were applied from a dropper bottle. After the wash drained into the membrane, another five drops of wash solution were applied and allowed to drain. Three drops of substrate solution containing 10 mM indoxyl phosphate (JBL Scientific, San Luis Obispo, Calif.), 200 mM 2-amino-2-methyl-1-propanol (JBL Scientific, San Luis Obispo, Calif.), 500 mM TRIS, pH 10.2, were added from a dropper bottle and the device was incubated for five minutes at room temperature. At the end of the incubation time the presence of a visually detectable purple to black line at the detection zone for toxin A was noted as a positive result. The absence of a visually detectable line at this zone was a negative result.

The sensitivity of this assay was measured by spiking toxin A (TechLab, Blacksburg Va.) into 5 ml volumes of sample diluent at 0.1, 0.05, 0.02, 0.01, and 0 ng/ml and performing the assay as described. The devices containing toxin A at 0.01 ng/ml and above exhibited faint but visible purple to black lines at the detection zone for toxin A. No visible line was present at the detection zone for toxin A in the device used to test the sample containing 0 ng/ml toxin A. Six patient samples were identified which had tested positive for *C. difficile* in a high-sensitivity glutamate dehydrogenase assay described in commonly assigned U.S. patent application Ser. No. 08/832,935, now U.S. Pat. No.

5,965,375, but were negative in previously available toxin A assays and had originally been determined to be negative by the toxin assay method employed at the laboratory that supplied the sample. These six samples were tested using the high sensitivity assay for toxin A and two of the samples resulted in clearly visible lines at the toxin A detection zone indicating positive results for the presence of toxin A. These results show that the assays of the present invention can detect target analytes in samples at concentrations substantially lower than can be detected using previously available methods.

Hybridomas or cells producing antibodies CD.TXA. 1.PC (ATCC 98388, Apr. 3, 1997), CD.43.9 (ATCC 98390, Apr. 3, 1997), CD.43.5.PC (ATCC 98389, Apr. 3, 1997), 3E12 (ATCC HB-12442, Dec. 5, 1997), and 7F11 (ATCC HB-12443, Dec. 5, 1997) were deposited with the American Type Culture Collection, Rockville, Md. under the Budapest Treaty on the dates indicated and given the Accession Nos. indicated.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A kit for detecting a target analyte in a sample, the kit comprising:
   a) a target analyte binding moiety that is capable of specifically binding the target analyte;
   b) a plurality of magnetically responsive particles to which are attached a plurality of capture moieties that are capable of reversibly binding the target analyte binding moiety; and
   c) a detection moiety that is capable of binding to the target analyte binding moiety or to a hapten present on the target analyte binding moiety.

2. The kit according to claim 1, wherein the magnetically responsive particles are magnetic latex beads.

3. The kit according to claim 1, wherein the target analyte binding moiety comprises a molecular tag.

4. The kit according to claim 3, wherein the molecular tag is selected from the group consisting of a decapeptide sequence, a polyhistidine sequence, and a FLAG peptide.

5. The kit according to claim 3, wherein the molecular tag is contained within an amino acid sequence that comprises an antibody.

6. The kit according to claim 5, wherein the amino acid sequence comprises an immunoglobulin heavy or light chain sequence.

7. The kit according to claim 1, wherein the target analyte is a polypeptide.

8. The kit according to claim 1, wherein the target analyte is a cell.

9. The kit according to claim 1, wherein the cell is a bacterial cell selected from the group consisting of an *E. coli* cell, a Salmonella cell, a Shigella cell, a Helicobacter cell, and a Campylobacter cell.

10. The kit according to claim 8, wherein the target analyte binding moiety binds to an outer membrane protein of a bacterial cell.

11. The kit according to claim 8, wherein the target analyte binding moiety binds to a lipopolysaccharide (LPS) of a bacterial cell.

12. The kit according to claim 1, wherein the target analyte binding moiety comprises an antibody.

13. The kit according to claim 1, wherein the target analyte binding moiety has sufficient affinity for the target analyte such that the target analyte binding moiety and the target analyte can immediately reassociate upon modification of a concentrated target analyte solution following exposure to conditions that cause dissociation of the target analyte binding moiety from the capture moieties.

14. The kit according to claim 1, wherein affinity of the target analyte binding moiety for the target analyte is such that the target analyte binding moiety and the target analyte remain associated throughout exposure to conditions that cause dissociation of the target analyte binding moiety from the capture moieties.

15. The kit according to claim 1, further comprising a solid support, other than the magnetically responsive particles, to which is attached a plurality of anchor moieties that can bind to the target analyte when the target complex is not bound to the magnetically responsive particles.

* * * * *